(12) United States Patent
Fritz-Langhals

(10) Patent No.: US 9,273,072 B2
(45) Date of Patent: Mar. 1, 2016

(54) METHOD FOR PRODUCING ORGANOSILICON COMPOUNDS WHICH HAVE AMINO GROUPS

(71) Applicant: Wacker Chemie AG, Munich (DE)

(72) Inventor: Elke Fritz-Langhals, Ottobrunn (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/396,362

(22) PCT Filed: Apr. 10, 2013

(86) PCT No.: PCT/EP2013/057456
§ 371 (c)(1),
(2) Date: Oct. 22, 2014

(87) PCT Pub. No.: WO2013/160104
PCT Pub. Date: Oct. 31, 2013

(65) Prior Publication Data
US 2015/0112092 A1    Apr. 23, 2015

(30) Foreign Application Priority Data
Apr. 27, 2012   (DE) .......................... 10 2012 207 062

(51) Int. Cl.
C07F 7/04       (2006.01)
C07F 7/18       (2006.01)
C08G 77/26      (2006.01)

(52) U.S. Cl.
CPC .............. C07F 7/1836 (2013.01); C08G 77/26 (2013.01)

(58) Field of Classification Search
CPC ............................ C07F 7/1836; C08G 77/26
USPC ....................................................... 556/413
See application file for complete search history.

(56) References Cited

U.S. PATENT DOCUMENTS

| 4,633,002 A | 12/1986 | Piskoti |
| 5,461,134 A | 10/1995 | Leir et al. |
| 6,284,860 B1 * | 9/2001 | Sommer .............. C09K 3/1018 528/23 |
| 7,238,768 B2 | 7/2007 | Hupfield et al. |
| 2005/0215806 A1 | 9/2005 | Heller et al. |
| 2006/0020097 A1 | 1/2006 | Briehn et al. |
| 2007/0299178 A1 | 12/2007 | Cook et al. |
| 2008/0009590 A1 | 1/2008 | Ziche et al. |
| 2011/0301374 A1 | 12/2011 | Selbertinger et al. |
| 2014/0238459 A1 | 8/2014 | Moors et al. |
| 2015/0112092 A1 | 4/2015 | Fritz-Langhals |

FOREIGN PATENT DOCUMENTS

| DE | 19733168 A1 | 2/1999 |
| DE | 102006031104 A1 | 1/2008 |
| EP | 0628589 A1 | 12/1994 |
| EP | 0739372 B1 | 12/1998 |
| EP | 1580215 A1 | 9/2005 |
| EP | 2841489 B1 | 8/2015 |
| JP | 2006-526668 A | 11/2006 |
| JP | 2008-511688 A | 4/2008 |
| JP | 2015-507454 A | 3/2015 |

OTHER PUBLICATIONS

International Search Report for PCT/EP2013/057456 dated Sep. 4, 2013.

* cited by examiner

*Primary Examiner* — Porfirio Nazario Gonzalez
*Assistant Examiner* — Kofi Adzamli
(74) *Attorney, Agent, or Firm* — Ceasar Rivise, PC

(57) ABSTRACT

The invention relates to a method for producing amino-functional polyorganosiloxanes, wherein (A) organosiloxanes which contain Si—OH groups are reacted with (B) at least stoichiometric quantities of mono-alkoxy(amino-alkyl)silanes, with respect to the Si—OH groups, (C) in the presence of at least one acid as a catalyst.

15 Claims, No Drawings

METHOD FOR PRODUCING ORGANOSILICON COMPOUNDS WHICH HAVE AMINO GROUPS

BACKGROUND OF THE INVENTION

The invention relates to a method for producing amino-containing organosilicon compounds having a minimal proportion of Si—OH and Si—OR moieties by use of (aminoalkyl)alkoxysilanes in the presence of catalysts.

Aminoalkylpolysiloxanes are widely used in industry. For instance, block copolymers are obtainable via polyaddition by use of isocyanates. A multiplicity of products having custom-tailored properties are thus obtainable by combining various polymeric blocks. Purity is very important for the aminoalkylpolysiloxanes used to construct block copolymers. Chain ends have to be highly amino-functionalized or high molecular weights cannot be achieved for the block copolymers.

Methods for preparing aminoalkylpolysiloxanes are already known. U.S. Pat. No. 5,461,134 describes an equilibration method involving use of 1,3-bis(3-aminopropyl)-tetramethyldisiloxane, cyclic siloxanes and tetramethylammonium hydroxide as catalyst. This method is inconvenient in that it requires long reaction times and the cyclic siloxanes have to be added in large excess and removed again after the reaction by stripping. This also holds for the similar method for preparing aminoalkylpolysiloxanes having higher molecular weights which is disclosed in EP-B-0739372. U.S. Pat. No. 4,633,002 describes a method for producing aminoalkylpolysiloxanes wherein silanol-terminated siloxanes are reacted with aminofunctional silanes in the presence of organometallic catalysts, in particular tin compounds. This method is disadvantageous on account of the required high temperatures of about 275° C. which, as reported therein, lead to yellowing of the reaction product due to decomposition processes. EP-A-0628589 describes a method for producing aminoalkylpolysiloxanes from silanol-terminated siloxanes, aminofunctional silanes and a combination between the catalysts barium hydroxide and/or strontium hydroxide on the one hand and sodium borate and/or sodium phosphate on the other. Especially the toxicity of the heavy metals barium and strontium is prejudicial to any industrial use of this method.

Equilibration reactions also have the in-principle disadvantage that the products obtained have a comparatively high silanol fraction. Si—OH chain ends act as chemically labile chain stoppers in a subsequent reaction with diisocyanates and thereby prevent the attainment of high molecular weights. A further disadvantage of unconverted Si—OH chain ends being present in the aminoalkylpolysiloxanes is that they can be the starting point for hydrolytic chain degradation. Materials of this type accordingly display lower stability in the presence of moisture.

US-A-2011/301374 describes a method whereby remaining Si—OH chain ends may be reacted with silazanes and thereby converted into the corresponding aminoalkyl groups. The achievement of high conversions, accordingly, requires two reaction steps.

U.S. Pat. No. 7,238,768 describes the production of aminofunctional polysiloxanes by reaction of hydroxyl-functional polysiloxanes with a deficiency of aminofunctional silanes, based on the Si—OH groups used, and in the presence of carboxylic acids. According to the prescription disclosed therein, the reaction of (aminoalkyl)alkoxysilane with the Si—OH groups is accompanied by an in situ reaction of the Si—OH groups with the added alcohol to form Si—O-alkyl groups. Since chain-stopping reactions with alkoxysilanes will always result in the formation of alcohols, generally highly reactive alcohols such as methanol or ethanol, it must be assumed that a similar reaction is occurring with the liberated alcohol.

As stated therein, the aminoalkylpolysiloxanes obtained all without exception contain both Si—OH and Si—O-alkyl groups.

According to the prescription disclosed in U.S. Pat. No. 7,238,768, the reaction of the (aminoalkyl)alkoxysilane with the Si—OH groups (the actual chain-stopping reaction) is also accompanied by a chain-extending reaction of Si—OH units with Si—OH units, which eliminates water and which is likewise catalyzed by the catalyst.

EP-A-1580215 further reports that the conditions disclosed in U.S. Pat. No. 7,238,768 result in the formation of products that have a yellow color and a short shelf life.

The method is accordingly unsuitable for producing amino-functional polysiloxanes having a minimal proportion of Si—O groups and Si—O-alkyl groups. Not only the Si—OH groups but also the Si—O-alkyl groups act as a labile chain stopper since the latter, when stored in the presence of atmospheric humidity, gradually convert into Si—OH groups by hydrolysis and liberate volatile alcohols in the process, while the Si—OH groups thus generated have the abovementioned disadvantages.

The method is also unsuitable for producing aminofunctional polysiloxanes having a constant molecular weight, since chain condensation results in the formation of products of distinctly increased molecular weight. But a constant chain length is very important for the abovementioned uses in block copolymers, since it is responsible for the physical properties of the materials obtained.

Yellowing and reduced shelf life likewise reduce product quality.

U.S. Pat. No. 6,284,860 describes the reaction of OH-terminated organo-polysiloxanes with di- and trialkoxy(aminoalkyl)silanes in the presence of Brønstedt or Lewis acids to form organopolysiloxanes containing about 30 to 60% of Si—O-alkyl groups.

According to the prescription given in U.S. Pat. No. 6,284,860, the reaction requires, based on the Si—OH groups present, at least stoichiometric amounts of the acid, which then remain in the reaction product as amine salts.

This method is accordingly unsuitable for producing amino-functional polysiloxanes having a minimal proportion of Si—O-alkyl groups. It is also unsuitable because the resultant high salt contents lead to inferior physical properties—such as rheology and visual transparency, for example—for the target products.

DESCRIPTION OF THE INVENTION

The invention provides a method for producing amino-functional polyorganosiloxanes which comprises reacting
(A) organosiloxanes which contain Si—OH groups with
(B) at least stoichiometric amounts of monoalkoxy(aminoalkyl)silanes, based on the Si—OH groups,
(C) in the presence of at least one acid as catalyst.

The inventors found that, surprisingly, aminoalkylpolysiloxanes having a minimal proportion of Si—OH groups and Si—O-alkyl groups are obtainable by reaction of hydroxypolysiloxanes (A) with at least stoichiometric amounts of monoalkoxy(aminoalkyl)silanes (B) in the presence of acidic catalysts.

The aminofunctional polyorganosiloxanes obtained preferably have a proportion of Si—OH groups and Si—O-alkyl groups of together less than 5 mol % based on the aminoalkyl groups.

The method of the invention is simple to carry out and leads to products of high purity. Concurrent reactions, such as the formation of Si—O-alkyl groups for example, only take place to a quite minimal extent. The chain length of the polysiloxane remains essentially unchanged except for the chain-stopping units which become attached. Chain condensation reactions only take place to an insignificant degree, if at all. The aminofunctional polysiloxanes obtained are clear and colorless. It is further advantageous that stoichiometric or minimal excesses of (aminoalkyl)alkoxysilane (B) are sufficient in the method of the invention to obtain products having a minimal proportion of Si—OH groups and Si—O-alkyl groups. The (aminoalkyl)alkoxysilanes (B) represent the costliest component in the production of aminoalkylpolysiloxanes, and so the method of the invention is particularly economical.

Preferably, aminofunctional polysiloxanes of general formula I

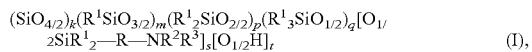
$$(SiO_{4/2})_k(R^1SiO_{3/2})_m(R^1{}_2SiO_{2/2})_p(R^1{}_3SiO_{1/2})_q[O_{1/2}SiR^1{}_2{-}R{-}NR^2R^3]_s[O_{1/2}H]_t \quad (I),$$

are obtained by reaction of organosiloxanes of general formula (II)

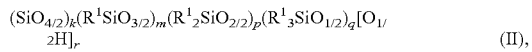
$$(SiO_{4/2})_k(R^1SiO_{3/2})_m(R^1{}_2SiO_{2/2})_p(R^1{}_3SiO_{1/2})_q[O_{1/2}H]_r \quad (II),$$

with at least the stoichiometric amount of a monoalkoxy-(aminoalkyl)silane of general formula (III)

$$R^2R^3N{-}R{-}SiR^1{}_2(OR^4) \quad (III),$$

in the presence of at least one Brønstedt or Lewis acid, where
R is an unsubstituted or halogen-substituted alkylene radical of 1 to 12 carbon atoms,
$R^x$ is hydrogen, an unsubstituted $C_1$-$C_{10}$ hydrocarbyl radical or a $C_1$-$C_{10}$ hydrocarbyl radical substituted with substituents selected from —CN and halogen,
$R^1$ is a hydrogen atom or a $C_1$-$C_{20}$ hydrocarbyl or $C_1$-$C_{15}$ hydrocarbyloxy radical which is bonded Si—C and is unsubstituted or substituted with substituents selected from —CN, $NR^x{}_2$, COOH, $COOR^x$, -halogen, -acryloyl, -epoxy, —SH, —OH and —$CONR^x{}_2$ and in each of which one or more mutually nonadjacent methylene units at a time may be replaced by groups —O—, —CO—, —COO—, —OCO— or —OCOO—, —S—, or $NR^x$ and in each of which one or more mutually nonadjacent methine units may be replaced by groups —N=, —N=N—, or —P=,
$R^2$ and $R^3$ are each hydrogen or unbranched, branched or cyclic saturated or unsaturated alkyl of 1 to 12 carbon atoms or aryl or aralkyl where individual nonadjacent methylene units may be replaced by nitrogen atoms or oxygen atoms,
$R^4$ is linear or branched alkyl of 1 to 8 carbon atoms where nonadjacent methylene units may be replaced by oxygens,
s is not less than 1,
r is not less than 1,
s+t is equal to the value of r, and
k+m+p+q is not less than 2,
and s:t is not less than 10.

Alkylene R may be unbranched, branched or cyclic, saturated or unsaturated. R is preferably a divalent unbranched or branched saturated alkylene radical of 1 to 8 carbon atoms, more preferably of 2 to 4, most preferably of 3, carbon atoms, more preferably an n-propylene group.

$R^1$ is preferably of 1 to 12 atoms, especially of 1 to 6 atoms, preferably carbon atoms only or one alkoxy oxygen atom and otherwise carbon atoms only. Preferably, $R^1$ is a straight-chain, branched or cyclic $C_1$-$C_6$ alkyl radical. The radicals methyl, ethyl, phenyl, vinyl and trifluoropropyl are particularly preferable.

Preferably, $R^2$ and $R^3$ are each independently hydrogen or unbranched, branched or cyclic saturated or unsaturated alkyl of 1 to 6 carbon atoms or aryl, where nonadjacent methylene units may be replaced by nitrogen atoms or oxygen atoms.

More preferably, $R^2$ and $R^3$ are each independently hydrogen or $C_1$-$C_5$ alkyl where individual nonadjacent methylene groups may be replaced by nitrogen atoms.

Most preferably, $R^2$ and $R^3$ are each hydrogen.

Preferably, $R^4$ is a linear or branched alkyl group of 1 to 5 carbon atoms where preferably 1 to 2 nonadjacent methylene units may be replaced by oxygens.

Alkyl groups of 1 to 5 carbon atoms are particularly preferable and it is particularly preferable for one methylene group to be replaced by oxygen.

Examples of radicals $R^4$ are methyl, ethyl, n-propyl, i-propyl, 2-methoxyethyl and 2-methoxypropyl.

Preferably, the proportion of Si—OH groups in the compounds of general formula I is minimal in relation to the proportion of aminofunctional alkyl groups. Preferably, the ratio s:t in general formula I is not less than 20 and more preferably not less than 50.

The aminofunctional organosiloxane of general formula I may be linear, cyclic or branched.

The sum of k, m, p, q, s and t is preferably a number from 3 to 20 000, especially from 8 to 1000.

Preferred branched organosiloxanes are the organosilicone resins which, in accordance with general formula I, contain T- and Q-units, i.e., k+m>0. Particular preference is given to resins wherein k+m is not less than 5% and not more than 90% based on the sum total of k, m, p, q, s and t.

Preferred linear aminofunctional organosiloxanes are the terminally aminofunctionalized organosiloxanes of general formula (Ia),

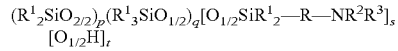
$$(R^1{}_2SiO_{2/2})_p(R^1{}_3SiO_{1/2})_q[O_{1/2}SiR^1{}_2{-}R{-}NR^2R^3]_s[O_{1/2}H]_t$$

where s+t+q=2,
where q may be 0 or 1.
p is preferably from 1 to 20 000, especially from 8 to 1000.

Particularly preferable linear aminofunctional organosiloxanes are the α,ω-terminally aminofunctionalized organosiloxanes where q=0 and s+t=2.

The catalyst used preferably comprises Brønstedt acids having $pK_a$ values between −10 and +5, for example halohydric acids, oxygen acids of elements from main groups 3 to 7, their acidic salts and acidic esters, where one or more oxygens may be replaced by halogen, e.g., carbonic acid, nitrous acid, nitric acid, phosphorous acid, alkali metal dihydrogenphosphite, mono- or diesters of phosphorous acid with $C_1$ to $C_{20}$ alcohols, phosphoric acid, alkali metal dihydrogenphosphate, mono- or diesters of phosphoric acid with $C_1$ to $C_{20}$ alcohols, sulfurous acid, sulfuric acid, alkali metal hydrogensulfate, monoesters of sulfuric acid with $C_1$ to $C_{20}$ alcohols, chloric acid and perchloric acid, bromic acid and perbromic acid, iodic acid and periodic acid, tetrafluoroboric acid, hexafluorophosphoric acid, $C_1$ to $C_{20}$ carboxylic acids, which may contain from 1 to 3 further carboxylic acid groups, organic carbon acids such as, for example, ascorbic acid and picric acid, oxygen acids of the elements sulfur and phosphorus that bear a $C_1$ to $C_{20}$ hydrocarbyl radical attached to sulfur or, respectively, phosphorus by a covalent bond, for example $C_1$ to $C_{20}$ sulfonic or phosphonic acids, amidosulfonic acids and amidophosphonic acids, iso- and heteropolyacids. Isopolyacids are condensates of inorganic polybasic acids having a single type of central atom, this single type of central atom being selected from Si, P, V, Mo and W, for example polymeric silicic acid, molybdic acid and tungstic acid. Heteropolyacids are inorganic polyacids having 2 or more differing central atoms from respectively polybasic oxygen acids of a metal, in particular Cr, Mo, V or W, and of a nonmetal, in particular As, I, P, Se, Si or Te, for example 12 molybdatophosphoric acid ($H_3[PMo_{12}O_{40}]$) or 12 tungstophosphoric acid ($H_3[PW_{12}O_{40}]$)

Examples further include carboxylated or sulfonated organic polymers, which may be linear, branched or crosslinked. The carboxyl or sulfonyl content of the polymers is preferably from 0.1 mol to 10 mol and more preferably from 1 mol to 5 mol of carboxylic or, respectively, sulfonic acid groups per kg of polymer.

The carboxylated and sulfonated organic polymers are preferably in a crosslinked state; that is, they are in the form of resins. The basic polymeric scaffold of the resins consists, for example, of polycondensates formed from phenol and formaldehyde, copolymers formed from styrene and divinylbenzene or copolymers formed from methacrylates and divinylbenzene. Preference is also given to sulfated alumina and acidic phyllosilicates, for example montmorillonites.

Preference is also given to Brønstedt-Lewis acid complexes, for example complexes between Lewis-acidic halides, for example $AlCl_3$, $PCl_3$, $PCl_5$, $FeCl_3$ or $ZnCl_2$ and water or amines. The complexes may also be formed in situ by reaction of the Lewis acid with the water present in the reaction mixture.

Brønstedt acids having $pK_a$ values between −10 and +2 are particularly preferable and between −10 and +1 are very particularly preferable.

When Brønstedt acids (proton donors) are used as catalysts, proton transfer to the basic aminofunctionalities in the compounds of general formulae I and III takes place, the degree of proton transfer depending on the particular acid-base equilibrium. The protonated compounds of general formulae Ia and IIIa

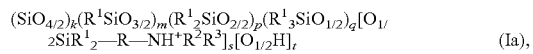

(Ia),

(IIIa), accordingly likewise represent catalysts for the purposes of the invention. R, $R^1$, $R^2$, $R^3$, $R^4$, k, m, p, q, s and t are each as defined for general formulae I and III.

Catalysts for the purposes of the invention also include the salts formed by protonation of nitrogen bases with the Brønstedt acids referred to.

Suitable nitrogen bases include amines $R^5R^6R^7N$, where the radicals $R^5$, $R^6$ and $R^7$ are each independently hydrogen or unbranched, branched or cyclic saturated or unsaturated alkyl of 1 to 12 carbon atoms or aryl or aralkyl, where individual nonadjacent methylene units may be replaced by nitrogen atoms or oxygen atoms. Examples thereof are ammonia, methylamine, ethylamine, ethylenediamine, dimethylamine, triethylamine, butylamine, diisobutylamine, aniline and N-methylaniline. The radicals may also be bonded to each other via carbon, oxygen or nitrogen atoms. Examples thereof are piperidine, piperazine, morpholine, pyrrolidine, 1,8-diazabicyclo[5.4.0]undec-7-ene, 1,5-diazabicyclo[4.3.0]non-5-ene, 1,4-diazabicyclo[2.2.2]octane.

Suitable nitrogen bases also include polyunsaturated nonaromatic or aromatically unsaturated heterocyclic nitrogen bases, for example pyridine, pyrimidine or imidazole.

Catalysts for the purposes of the invention also include Brønstedt-Lewis acid complexes, for example complexes between Lewis-acidic halides, for example $AlCl_3$, $PCl_3$, $PCl_5$, $FeCl_3$ or $ZnCl_2$ and water or amines.

The complexes may also be formed in situ by reaction of the Lewis acid with the water present in the reaction mixture.

Examples of the acids used are hydrogen chloride, hydrogen bromide, perchloric acid, sulfuric acid, methyl sulfate, methanesulfonic acid, benzenesulfonic acid, trifluoromethanesulfonic acid, tetrafluoroboric acid, phosphoric acid, nitric acid, chloroacetic acid, dichloroacetic acid, trichloroacetic acid, trifluoroacetic acid, benzoic acid, phthalic acid, oxalic acid, malonic acid, succinic acid, fumaric acid, maleic acid and their ammonium salts, for example ammonium chloride, ammonium sulfate, methylammonium chloride, triethylammonium chloride, ammonium trifluoromethanesulfonate and ammonium trifluoroacetate.

The acids are used in amounts of not more than 20 weight percent, preferably not more than 10 weight percent, more preferably of not more than 1 weight percent and most preferably of 0.1% and not less than 0.1 ppm, preferably not less than 1 ppm, more preferably not less than 5 ppm and most preferably of not less than 10 ppm, all based on the entire reaction mass.

Temperatures at which the method is carried out are preferably not less than 50° C. and more preferably not less than 90° C. and not more than 200° C. and more preferably not more than 150° C.

The method is preferably carried out under atmospheric pressure or under reduced pressure. Particularly preferred pressures range between not more than 500 mbar and 1 mbar.

The method of the invention may be carried out as a batch reaction, as a semi-batch reaction or in a continuous manner. For example, the reaction components may be mixed at ambient temperature and the mixture heated to the reaction temperature. In a further preferred embodiment, the catalyst is mixed with the monoalkoxy(aminoalkyl)silane (B) and this is added to the organosiloxane (A).

The reaction is preferably carried out by commixing. Methods of mixing which are familiar to a person skilled in the art may be employed here. Stirring may be used to effect the commixing for example.

In one preferred embodiment, the alcohol liberated in the course of the reaction is removed from the reaction mixture during or after the reaction. Removal is preferably effected by distillation, for example by distillation under reduced pressure. Distillation techniques familiar to a person skilled in the art may be used for this purpose, examples being equilibrium distillation through a column, short path distillation or thin film evaporation.

The reaction of the invention may also be carried out in a continuous manner. Technical implementations familiar to a person skilled in the art are suitable here, examples being tubular reactors, loop reactors or stirred tank batteries.

The monoalkoxy(aminoalkyl)silane (B) is preferably used in a molar amount of not less than 1.01 and not more than 10 equivalents based on Si—OH units present, more preferably in molar proportions of not less than 1.05 and not more than equivalents, based on Si—OH units present in the organosiloxane (A).

A computation of the excess in which the (aminoalkyl)alkoxy-silane (B) used has to be used to achieve complete conversion must take account of the amount of water present in the hydroxypolysiloxane (A), since the (aminoalkyl)alkoxysilane (B) is consumed by water to form the corresponding disiloxane. This is simple to remove by devolatilizing the reaction mixture after the reaction.

The reaction may utilize further components, for example solvents, in amounts of not less than 1% and not more than 200%, preferably not less than 10% and not more than 100%, based on the overall reaction mass. When solvents are used, the preference is for solvents or solvent mixtures having a boiling point/range of up to 120° C. at 0.1 MPa. Examples of solvents include ethers such as methyl tert butyl ether, tetrahydrofuran or dioxane, nitriles such as acetonitrile or propionitrile, DMSO, hydrocarbons such as, for example, heptane, methylcyclohexane or toluene.

The above symbols in the above formulae each all have their meanings independently of each other. The silicon atom is tetravalent in all formulae.

In the examples which follow, amounts and percentages are all by weight, pressures are all 0.10 MPa abs. and temperatures are all 20° C., unless specifically stated otherwise.

The examples are all carried out under inertization and/or protective gas.

EXAMPLE 1

330 g of α,ω-bishydroxy-terminated polydimethylsiloxane having an $M_n$ of 2320 g/mol, as determined by $^1$H NMR spectroscopy, corresponding to 284 mmol of Si—OH groups, and a water content of 250 ppm, corresponding to 4.6 mmol, as determined by Karl Fischer titration, is admixed with 6 mg of ammonium chloride and heated to 108-112° C. At this temperature and about 100 mbar pressure, 46.01 g (305 mmol, corresponding to 1.07 equivalents based on Si—OH) of 97.5 percent 3-aminopropyldimethylmethoxysilane 1 are added over 18 min, and the methanol formed is collected as distillate in a cooled receiver. Following an overall reaction time of 2 hours, the reaction product—the α,ω-bisaminopropyl-terminated polydimethylsiloxane—is analyzed by NMR spectroscopy. What is detected is Si—OH end groups at 0.2%, Si—OMe groups at 0.06%, methanol at 2.3% and silane 1 at 3.7%, all based on the molar amount of aminopropyl end groups.

The product obtained is 10.1 g of distillate consisting of methanol at 97.6% and a mixture of silane 1 and cyclic siloxanes at 2.4% (0.24 g).

The pressure is lowered to about 1 mbar to remove excess silane 1 and methanol from the product.

EXAMPLE 2

Example 1 is repeated using 3 mg of ammonium chloride and 46.1 g (306 mmol, 1.08 equivalents) of 97.6 percent silane 1. The overall reaction time is 3 hours.

The reaction product at the end of the reaction contains, based on the molar amount of aminopropyl end groups, 0.2% of Si—OH end groups, 2.2% of methanol and 3.2% of silane 1. Si—OMe end groups are not detectable (detection limit about 0.1%).

The product obtained is 9.8 g of distillate consisting of methanol at 98% and of a mixture of silane 1 and cyclic siloxanes at 2.0% (0.20 g).

The pressure is lowered to about 1 mbar to remove excess silane 1 and methanol from the product.

EXAMPLE 3

330 g of α,ω-bishydroxy-terminated polydimethylsiloxane having an $M_n$ of 2320 g/mol, as determined by H NMR spectroscopy, corresponding to 284 mmol of Si—OH groups, and a water content of 250 ppm, corresponding to 4.6 mmol, as determined by Karl Fischer titration, 6 mg of ammonium chloride and 46.01 g (305 mmol, corresponding to 1.07 equivalents based on Si—OH) of 97.5 percent 3-aminopropyldimethylmethoxysilane 1 are mixed at room temperature and heated to 110° C. at about 110 mbar with stirring while methanol is distilled off into a cooled receiver. The heating time is 22 min, the overall reaction time is 2 hours.

The reaction product at the end of the reaction contains, based on the molar amount of aminopropyl end groups, 0.6% of Si—OH end groups, 2.3% of methanol and 3.6% of silane 1. Si—OMe end groups are not detectable (detection limit about 0.1%).

The product obtained is 10.0 g of distillate consisting of methanol at 98% and of a mixture of silane 1 and cyclic siloxanes at 2.0% (0.20 g).

The pressure is lowered to about 1 mbar to remove excess silane 1 and methanol from the product.

EXAMPLE 4

110 g of α,ω-bishydroxy-terminated polydimethylsiloxane having an $M_n$ of 2366 g/mol, as determined by $^1$H NMR spectroscopy, corresponding to 93.0 mmol of Si—OH groups, and a water content of 300 ppm, corresponding to 1.8 mmol, as determined by Karl Fischer titration, is heated to 108-112° C. At this temperature and about 100 mbar pressure 14.3 g (96.1 mmol, corresponding to 1.03 equivalents, based on Si—OH) of 99 percent 3-aminopropyldimethylmethoxysilane 1 containing 1.1 mg of ammonium chloride in solution are added over 10 min and the methanol formed is collected as distillate in a cooled receiver. Following an overall reaction time of 1.5 (3 hours), the reaction product—the α,ω-bisaminopropyl-terminated polydimethylsiloxane—is analyzed by NMR spectroscopy. What is detected is Si—OH end groups at 0.35% (0.19%), Si—OMe groups at 0.02% (0.03%), methanol at 3.2% (2.3%) and silane 1 at 3.5% (1.0%), all based on the molar amount of aminopropyl end groups. The product obtained is 2.9 g of distillate.

EXAMPLE 5

551 g of α,ω-bishydroxy-terminated polydimethylsiloxane having an $M_n$ of 2366 g/mol, as determined by $^1$H NMR spectroscopy, corresponding to 466 mmol of Si—OH groups, and a water content of 300 ppm, corresponding to 9.2 mmol, as determined by Karl Fischer titration, are heated under Ar at a heating rate of 40° C. per hour at about 100 mbar while being admixed with 76.8 g (512 mmol, corresponding to 1.06 equivalents based on Si—OH having regard to the losses of 1 by reaction with water) of 98.2 percent aminopropyldimethylmethoxysilane 1 containing the catalyst (particulars regarding catalyst see table 1) in solution. The addition of the silane is complete after about 20 min. During the reaction, the methanol formed is distilled off. After 140 min a temperature of 130° C. is reached. At this temperature, the reaction is allowed to continue for a further hour, at which point the reaction mixture is cooled down. The amount of distillate obtained at the end of the run is about 16 g.

To devolatilize the crude product obtained, it is devolatilized in a thin film evaporator.

Kinetic trajectory of reaction and product composition see table 1.

The proportions of reactants and products were determined by $^1$H NMR spectroscopy in d6-benzene.

TABLE 1

Chain-stopping reactions (conditions see Example 5) with various catalysts and catalyst quantities.

| Catalyst | Amount[1] (ppm) | Reaction time[2] t (min) | Si—OH (mol %)[3] | Si—OMe (mol %)[3] | Silane 1 (mol %)[3] | MeOH (mol %)[3] |
|---|---|---|---|---|---|---|
| NH$_4$Cl | 20 | 154 | 1.94 | <0.1 | 5.7 | 14.2 |
|  |  | 180 | 0.24 | <0.1 | 4.2 | 9.7 |
|  |  | 240 | 0.08 | <0.1 | 3.9 | 1.4 |
|  |  | after thin filming | 0.03 | ~0.1 | 0.1 | 0.1 |
| NH$_4$Cl | 40 | 152 | 0.60 | <0.1 | 3.9 | 2.6 |
|  |  | 170 | 0.13 | <0.1 | 3.4 | 1.9 |
|  |  | 230 | 0.06 | <0.1 | 3.2 | 1.3 |
|  |  | after thin filming | 0.03 | ~0.1 | 0.1 | 0.09 |
| NH$_4$Cl | 60 | 135 | 1.17 | <0.1 | 5.0 | 3.9 |
|  |  | 152 | 0.22 | <0.1 | 4.0 | 2.5 |
|  |  | 167 | 0.07 | <0.1 | 4.1 | 2.0 |
|  |  | 237 | 0.06 | <0.1 | 3.8 | 1.5 |
|  |  | after thin filming | 0.02 | 0.09 | 0.1 | 0.05 |
| NH$_4$Cl | 80 | 140 | 0.29 | <0.1 | 5.8 | 3.0 |
|  |  | 157 | 0.06 | <0.1 | 5.6 | 2.2 |
|  |  | 170 | 0.04 | <0.1 | 5.2 | 2.0 |
|  |  | 230 | 0.03 | <0.1 | 3.8 | 2.5 |
|  |  | after thin filming | 0.008 | 0.16 | 0.3 | 0.03 |
| CH$_3$SO$_3$H | 40 | 165 | 0.44 | 0.07 | 6.2 | 2.6 |
|  |  | 225 | 0.07 | <0.1 | 3.6 | 1.9 |
|  |  | after thin filming | 0.03 | 0.06 | 0.13 | 0.04 |
| CH$_3$SO$_3$H | 60 | 135 | 3.00 | <0.1 | 5.9 | 2.9 |
|  |  | 152 | 1.03 | <0.1 | 4.7 | 2.7 |
|  |  | 165 | 0.23 | <0.1 | 3.7 | 1.8 |
|  |  | 235 | 0.06 | <0.1 | 3.7 | 1.4 |
|  |  | after thin filming | 0.01 | <0.1 | 0.27 | 0.04 |
| CF$_3$COOH | 60 | 153 | 2.3 | 0.09 | 6.00 | 2.78 |
|  |  | 170 | 0.97 | 0.11 | 5.0 | 2.5 |
|  |  | 230 | 0.097 | 0.11 | 4.2 | 1.4 |
|  |  | after thin filming |  |  |  |  |
| CCl$_3$COOH | 600 | 150 | 3.2 | 0.08 | 6.5 | 2.7 |
|  |  | 170 | 1.1 | 0.07 | 4.7 | 2.1 |
|  |  | 230 | 0.06 | 0.09 | 3.5 | 1.4 |
|  |  | 290 | 0.03 | 0.12 | 3.3 | 0.8 |
|  |  | after thin filming | 0.02 | 0.16 | 0.04 | 0.02 |

[1] based on overall reaction mass;
[2] at a heating rate of 40° C./hour to 130° C.;
[3] based on the molar proportion of aminoalkyl groups of the aminopropylpolysiloxane.

EXAMPLE 6

558 g of α,ω-bishydroxy-terminated polydimethylsiloxane having an $M_n$ of 2366 g/mol, as determined by $^1$H NMR spectroscopy, corresponding to 466 mmol of Si—OH groups, and a water content of 300 ppm, corresponding to 9.2 mmol, as determined by Karl Fischer titration, are heated under Ar at a heating rate of 30° C. per hour up to about 100° C. while being admixed with 78.0 g (520 mmol, corresponding to 1.06 equivalents based on Si—OH having regard to the losses of 1 by reaction with water) of 98.2 percent aminopropyldimethylmethoxysilane 1 containing 38.2 mg ammonium chloride in solution. The addition of the silane is complete after about 20 min. On attaining the final temperature of 100° C. the methanol formed boils under reflux. The reflux condenser is replaced with a distillation bridge and heating is continued up to 130° C. with the methanol formed passing over as distillate. After a further hour at 130° C., the reaction mixture is cooled down and analyzed by $^1$H NMR spectroscopy. Contents in mol % based on the molar fraction of aminoalkyl groups of the aminopropylpolysiloxane: Si—OH: 1.2%, Si—OMe: 0.6%, silane 1:5.5%, methanol: 24%.

What is claimed is:

1. A method for producing aminofunctional polyorganosiloxanes which comprises reacting
   (A) organosiloxanes which contain Si—OH groups with
   (B) at least stoichiometric amounts of monoalkoxy(aminoalkyl)silanes, based on the Si—OH groups,
   (C) in a presence of at least one acid as catalyst,
   wherein a sum of a proportion of Si—OH groups and a proportion of Si—O-alkyl groups of the aminofunctional polyorganosiloxanes is less than 5 mol % based on aminoalkyl groups.

2. The method as claimed in claim 1 wherein aminofunctional polysiloxanes of general formula I

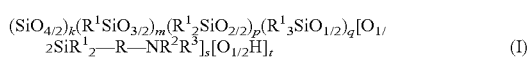   (I)

are obtained by reaction of organosiloxanes of general formula (II)

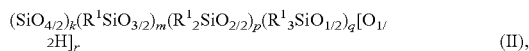
(II), with at least the stoichiometric amount of a monoalkoxy(aminoalkyl)silane of general formula (III)

(III), in the presence of at least one Brønstedt or Lewis acid, where

R is an unsubstituted or halogen-substituted alkylene radical of 1 to 12 carbon atoms, $R^x$ is hydrogen, an unsubstituted $C_1$-$C_{10}$ hydrocarbyl radical or a $C_1$-$C_{10}$ hydrocarbyl radical substituted with substituents selected from —CN and halogen, $R^1$ is a hydrogen atom or a $C_1$-$C_{20}$ hydrocarbyl or $C_1$-$C_{15}$ hydrocarbyloxy radical which is bonded Si—C and is unsubstituted or substituted with substituents selected from —CN, $NR^x_2$, COOH, COM', -halogen, -acryloyl, -epoxy, —SH, —OH and —$CONR^x_2$ and in each of which one or more mutually nonadjacent methylene units at a time may be replaced by groups —O—, —CO—, —COO—, —OCO— or —OCOO—, —S—, or Me and in each of which one or more mutually nonadjacent methine units may be replaced by groups —N=, —N=N—, or —P=, $R^2$ and $R^3$ are each hydrogen or unbranched, branched or cyclic saturated or unsaturated alkyl of 1 to 12 carbon atoms or aryl or aralkyl where individual nonadjacent methylene units may be replaced by nitrogen atoms or oxygen atoms, $R^4$ is linear or branched alkyl of 1 to 8 carbon atoms where nonadjacent methylene units may be replaced by oxygens, s is not less than 1, r is not less than 1, s+t is equal to the value of r, and k+m+p+q is not less than 2, and s:t is not less than 10.

3. The method as claimed in claim 2 wherein R is a divalent unbranched alkylene radical of 1 to 8 carbon atoms.

4. The method as claimed in claim 2 wherein $R^1$ is a straight-chain, branched or cyclic $C_1$-$C_6$ alkyl radical.

5. The method as claimed in claim 2 wherein $R^2$ and $R^3$ are each hydrogen.

6. The method as claimed in claim 2 wherein $R^4$ is alkyl of 1 to 5 carbon atoms.

7. The method as claimed in claim 1 wherein the catalyst used comprises Brønstedt acids having $pK_a$ values between −10 and +5.

8. The method as claimed in claim 1 conducted at temperatures of 50° C. to 150° C.

9. The method as claimed in claim 1 wherein said monoalkoxy(aminoalkyl)silane is used in a molar amount of not less than 1.01 and not more than 10 equivalents based on Si—OH units present in said organosiloxane.

10. The method as claimed in claim 3 wherein $R^1$ is a straight-chain, branched or cyclic $C_1$-$C_6$ alkyl radical.

11. The method as claimed in claim 10 wherein $R^2$ and $R^3$ are each hydrogen.

12. The method as claimed in claim 11 wherein $R^4$ is alkyl of 1 to 5 carbon atoms.

13. The method as claimed in claim 12 wherein the catalyst used comprises Brønstedt acids having $pK_a$ values between −10 and +5.

14. The method as claimed in claim 13 conducted at temperatures of 50° C. to 150° C.

15. The method as claimed in claim 14 wherein said monoalkoxy(aminoalkyl)silane is used in a molar amount of not less than 1.01 and not more than 10 equivalents based on Si—OH units present in said organosiloxane.

* * * * *